(12) United States Patent
Krumpelmann et al.

(10) Patent No.: US 11,540,919 B2
(45) Date of Patent: Jan. 3, 2023

(54) LOW PROFILE RIBBON FRAME FOR VALVE REPAIR DEVICES

(71) Applicant: Boston Scientific Scimed, Inc., Maple Grove, MN (US)

(72) Inventors: Graham Krumpelmann, Stillwater, MN (US); Joshua M. Inouye, Maple Grove, MN (US); James M. Anderson, Corcoran, MN (US); John M. Edgell, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 17/125,137

(22) Filed: Dec. 17, 2020

(65) Prior Publication Data

US 2021/0220136 A1   Jul. 22, 2021

Related U.S. Application Data

(60) Provisional application No. 62/963,786, filed on Jan. 21, 2020.

(51) Int. Cl.
  *A61F 2/24*  (2006.01)
  *A61L 27/04* (2006.01)

(52) U.S. Cl.
  CPC .... *A61F 2/2445* (2013.01); *A61F 2210/0014* (2013.01); *A61F 2220/0016* (2013.01); *A61F 2220/0025* (2013.01); *A61F 2230/0091* (2013.01); *A61F 2250/001* (2013.01); *A61F 2250/0007* (2013.01); *A61L 27/042* (2013.01)

(58) Field of Classification Search
  CPC .... A61F 2/2442–2448; A61F 2250/001; A61F 2210/0014; A61F 2220/0008–0016; A61B 2017/00243
  See application file for complete search history.

(56) References Cited

U.S. PATENT DOCUMENTS

| 9,622,862 B2 | 4/2017 | Lashinski et al. |
| 2011/0166649 A1* | 7/2011 | Gross .................... A61F 2/2466 623/2.36 |
| 2013/0123910 A1 | 5/2013 | Cartledge et al. |
| 2014/0031929 A1 | 1/2014 | Cartledge et al. |
| 2017/0135816 A1 | 5/2017 | Lashinski et al. |

OTHER PUBLICATIONS

International Search Report and Written Opinion for the International Patent Application No. PCT/US2020/065573, dated Mar. 16, 2021, 27 pages.

* cited by examiner

*Primary Examiner* — Rebecca S Preston
(74) *Attorney, Agent, or Firm* — Seager, Tufte & Wickhem LLP

(57) ABSTRACT

A low profile implant, system and method of deployment includes a frame comprising an elongate body having ends that overlap to form an annular configuration of the frame. A circumference of the frame may be modified by varying an extent of the overlap between the ends of the elongate body. The elongate structure may extend through a sleeve of a number of respective anchor housings of the implant along a first axis, and anchors may be deployed through bores in the anchor housings along a second axis to secure the anchor housings to tissue. The implant may be deployed about and anchored to a valve annulus, and the circumference of the frame, and associated anchored tissue, may be adjusted to reconfigure the valve annulus.

16 Claims, 13 Drawing Sheets

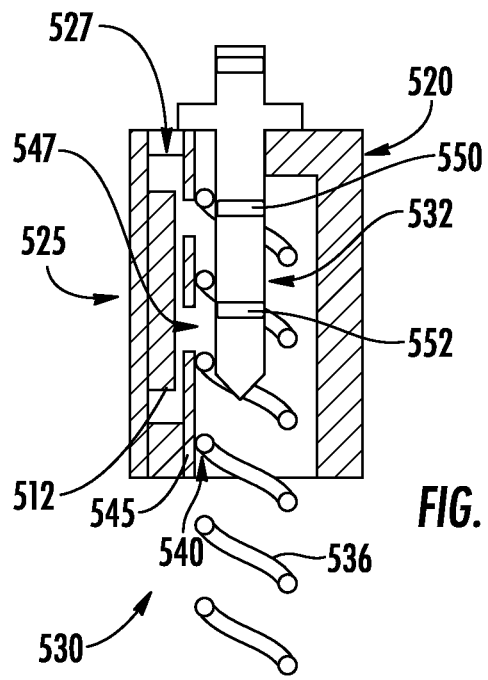
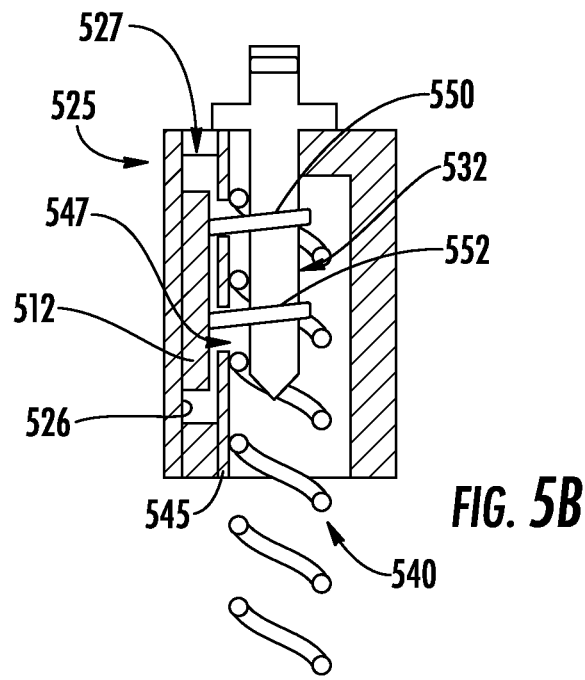
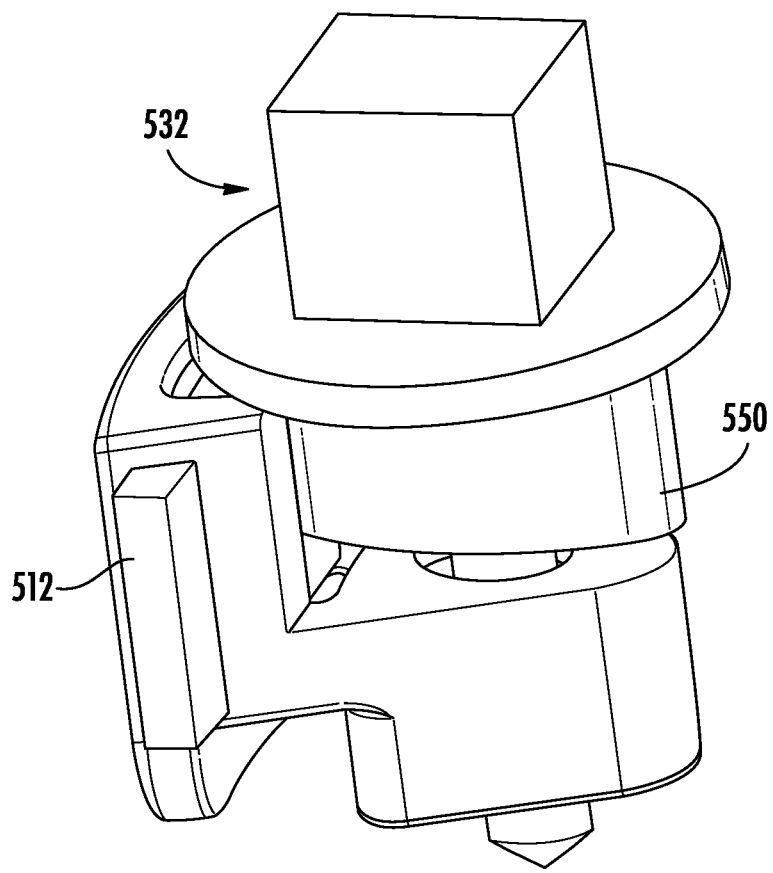

LOW PROFILE RIBBON FRAME FOR VALVE REPAIR DEVICES

CROSS-REFERENCE TO RELATED APPLICATIONS

The present application claims the benefit of priority under 35 U.S.C. § 119 to U.S. Provisional Patent Application 62/963,786, filed Jan. 21, 2020, which application is incorporated herein by reference in its entirety for all purposes.

FIELD

The present disclosure relates generally to the field of implantable medical devices. In particular, the present disclosure relates to medical devices, systems, and methods for annuloplasty and other cardiac treatment techniques.

BACKGROUND

Mitral insufficiency (MI) (also referred to as mitral regurgitation or mitral incompetence) is a form of heart disease where the mitral annulus dilates excessively and the valve leaflets no longer effectively close, or coapt, during systolic contraction. Regurgitation of blood occurs during ventricular contraction and cardiac output may decrease as a result. Surgical and endoluminal annuloplasty techniques have been introduced that aim to restore a mitral valve to its native configuration, for example by implanting an annuloplasty ring around a valve annulus. One problem encountered by such implants is that their size may cause unintended contact between the implant and the cardiac wall, reducing the efficacy of the implant. It is desirable to minimize the size of an implant to reduce the opportunity for such contact and it is with these considerations in mind that the improvements of the present disclosure may be useful.

SUMMARY

Embodiments of the present disclosure relate to a system, device and method for reshaping a valve annulus such as a heart valve annulus. According to one aspect, an implant includes a frame including an elongate body having an annular configuration with an adjustable circumference, an anchor housing including a sleeve extending through the anchor housing along a first axis and a bore extending through the anchor housing along a second axis different from the first axis, where the elongate body of the frame is translatably disposed within the sleeve of the frame. The implant includes an adjustment mechanism configured to adjust the adjustable circumference of the frame.

In various embodiments, the implant may include an anchor translatably disposed within the bore of the anchor housing. The implant may further include a retention mechanism configured to retain the frame at the adjusted circumference by inhibiting translation of the elongate body through the sleeve of the anchor housing by securing the elongate body between an internal wall of the sleeve of the anchor housing and the retention mechanism. In one embodiment, the retention mechanism includes a cam lock disposed about the anchor and having a locked configuration where a cam arm of the cam lock urges the elongate body towards a sidewall of the sleeve to inhibit translation of the elongate body through the sleeve. In one embodiment, the anchor includes a proximal shaft and the retention mechanism includes a ledge that extends radially from the proximal shaft towards the sleeve and an arm, extending distally from the ledge, the arm aligned with the sleeve and configured to extend into the sleeve when the ledge is distally translated to urge the elongate body towards an end wall of the sleeve to inhibit translation of the elongate body through the sleeve.

In one embodiment, the elongate body includes a plurality of grooves disposed at least partially along at least one surface, and the adjustment mechanism includes a gear having a plurality of teeth extending into the sleeve of the anchor housing, where actuation of the gear engages the plurality of teeth of the gear with the plurality of grooves of the elongate body to translate the elongate body through the sleeve. In one embodiment, the anchor housing is one of a plurality of anchor housings of the implant, the elongate body extends through each of the anchor housings of the plurality of anchor housings, and at least one of the anchor housings includes the gear. In one embodiment, the elongate body includes a ribbon frame, and the ribbon frame is comprised of stainless steel, a shaped memory alloy, a polymer or a combination thereof, the ribbon frame having a first end and a second end that overlap in the annular configuration, where the adjustable circumference is based on an extent of overlap between the first end and the second end. In one embodiment, the ribbon frame includes a first compressed configuration enabling the frame to be transluminally advanced to a treatment site and an expanded configuration including an annulus repair circumference selected to position the ribbon frame about a valve annulus. In some embodiments, the implant further includes an expansion mechanism configured to expand the ribbon frame to an anchoring circumference larger than the annulus repair circumference. In some embodiments, the ribbon frame includes at least one blunted edge, at least one stress diffusion feature or combination thereof According to another aspect, an implant includes a plurality of anchor housings, each anchor housing including a sleeve and a bore extending therethrough, where the sleeve extends through the anchor housing along a first axis, and the bore extends through the anchor housing along a second axis, different from the first axis. The implant includes a plurality of anchors, each anchor extending through one of the plurality of anchor housings, each anchor including a sharpened distal tip and a frame including an elongate body extending through each sleeve of each anchor housing, the elongate body including an annular configuration configured to position the plurality of anchor housings supported by the frame about a valve annulus. The implant further includes an adjustment mechanism configured to adjust a circumference of the frame.

In various embodiments, the implant includes a retention mechanism disposed within at least one anchor housing and configured to inhibit translation of the elongate body through the plurality of anchor housings. In some embodiments, the elongate body is comprised of stainless steel, a shaped memory alloy, a polymer or a combination thereof, and includes a first end and a second end that overlap in the annular configuration, where the circumference of the frame is based on an extent of overlap between the first end and the second end. In one embodiment, the elongate body includes a plurality of grooves disposed at least partially along at least one surface, the adjustment mechanism is disposed in at least one anchor housing and includes a gear having a plurality of teeth, and actuation of the gear engages the plurality of teeth of the gear with the plurality of grooves of the elongate body to translate the elongate body through the sleeve.

In one embodiment, the implant further includes a retention mechanism configured to retain the frame at an adjusted circumference by inhibiting translation of the elongate body through at least one sleeve of at least one anchor housing by securing the elongate body between an internal wall of the at least one sleeve of the at least one anchor housing and the retention mechanism. The retention mechanism may include a cam lock disposed about the anchor and having a locked configuration where a cam arm of the cam lock urges the elongate body towards a sidewall of the at least one sleeve to inhibit translation of the elongate body through the at least one sleeve. In one embodiment, at least one anchor associated with at least one anchor housing includes a proximal shaft disposed along the second axis, and the retention mechanism includes a ledge that extends radially from the proximal shaft towards a sleeve of the at least one anchor housing, and an arm, extending distally from the ledge, the arm aligned with the sleeve and configured to extend into the sleeve when the ledge is distally translated to urge the elongate body towards an end wall of the at least one anchor housing to inhibit translation of the elongate body through the sleeve.

According to another aspect, a method of valvular repair includes the steps of advancing a distal end of a delivery catheter to a valve treatment site, the distal end of the delivery catheter having an implant disposed therein and releasing the implant from the distal end of the delivery catheter. The implant includes a plurality of anchor housings, each anchor housing including a sleeve extending therethrough and a frame including an elongate body threaded through each sleeve of the plurality of anchor housings, where ends of the elongate body overlap through at least some of the sleeves of the plurality of anchor housings. The method includes the steps of expanding the frame to position the anchor housings about a valve annulus, driving the anchors into the valve annulus, adjusting a circumference of the frame to an annular reconfiguration circumference; and securing the frame within at least one sleeve of at least one anchor housing to inhibit translation of the elongate body through the at least one sleeve to retain the annular reconfiguration circumference of the frame.

According to one embodiment, at least one anchor housing includes a gear including a plurality of teeth, and at least a portion of the elongate body includes a plurality of grooves, and the step of adjusting the circumference includes the steps of actuating the gear to engage grooves of the elongate body to move the elongate body through the anchor housing.

With such an arrangement, a low-profile valve annulus implant with increased flexibility and a reduced potential for inadvertent contact with cardiac tissue is provided.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical illustrated component is typically represented by a single numeral. For purposes of clarity, not every component is labeled in every figure, nor is every component of each embodiment shown where illustration is not necessary to allow those of ordinary skill in the art to understand the disclosure. In the figures:

FIGS. 5A and 5B are cross-sectional views of an anchor housing illustrating one embodiment of a frame retention mechanism as disclosed herein;

FIG. 5C is an enlarged perspective view of a portion of the frame retention mechanism of FIGS. 5A and 5B.

DETAILED DESCRIPTION

A low profile implant, system and method of deployment, as disclosed herein in various embodiments, includes a frame comprising a ribbon shaped elongate body that is generally annular (e.g. circular, ovoid) in form and configured for custom reshaping of the heart valve. In one embodiment the elongate body may be threaded through a plurality of anchor housings, for example for free movement of the elongate body within sleeves of the anchor housings. The anchor housings may support anchors that may be used to anchor the anchor housings and the frame to valvular tissue. In one embodiment, the frame may be adjusted to increase and/or decrease a circumference of the frame, for example to expand the circumference of the frame for anchoring the frame about a valve annulus and/or for cinching the frame to reduce a circumference of a valve annulus to which the frame is anchored. In some embodiments, the frame may be formed of a shaped memory material that automatically assumes a cinched configuration for annular reshaping. In such embodiments, adjustment mechanisms may include expansion mechanisms (such as balloons and the like), to expand a circumference of the frame for anchoring purposes.

In some embodiments, adjustment mechanisms for increasing and/or decreasing a circumference of the frame may be included within one or more of the anchor housings. For example, some frames may be formed from an elongate body biased in an annular configuration and having overlapping ends. Adjustment mechanisms may be provided that modify the circumference of the frame by increasing or decreasing an extent of overlap of the ends of the frame. Such adjustment mechanisms, for example, may include gears comprising teeth that interact with grooves disposed on a surface of the frame to translate the elongate body through the sleeves of the anchor housings to achieve a selected annular reconstruction. Retention mechanisms may be provided by the anchors and/or anchor housing to inhibit further translation of the elongate member through the sleeves of the anchor housings, to secure the implant in the reconstructed configuration.

These and other beneficial aspects of an implant and method of deployment are described in more detail below. Although embodiments of the present disclosure may be described with specific reference to mitral valves, the principles disclosed herein may be readily adapted to facilitate reconstruction of any valve annulus, for example including a tricuspid valve annulus and/or may similarly benefit any other dilatation, valve incompetency, valve leakage, and other similar heart failure conditions.

As used herein, the term "distal" refers to the end farthest away from the medical professional when introducing a medical device into a patient, while the term "proximal" refers to the end closest to the medical professional when introducing a medical device into a patient.

Figure 1:
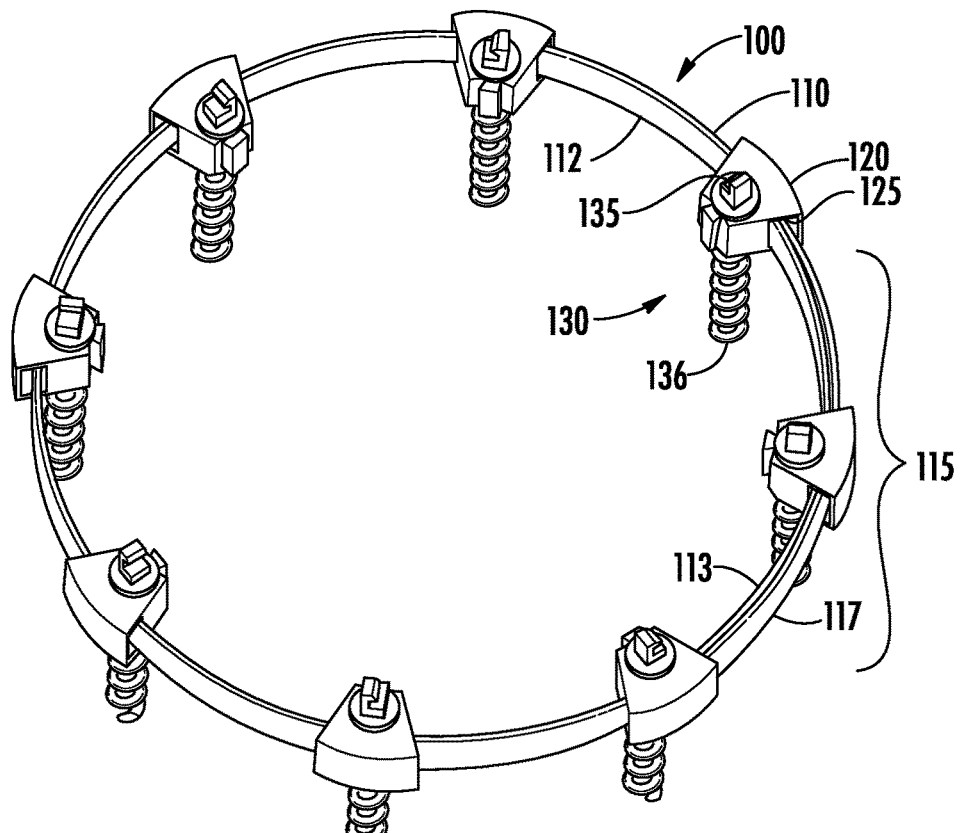
FIG. 1 is a diagram of one embodiment of an implant comprising a generally ribbon shaped, annular frame having an adjustable circumference as disclosed in various embodiments herein.

FIG. 1 illustrates an implant 100 comprising a frame 110 that may be disposed about a heart valve or other cardiac feature. For purposes of clarity, not all the components of the implant are numbered. In one embodiment, the frame 110 may extend circumferentially around a central frame axis extending proximally-distally through a center point of the frame. The frame 110 may be generally symmetric with respect to the central frame axis although it need not be symmetric. The frame 110 may be comprised of a generally ribbon shaped elongate body 112 that is generally annular in shape, where herein "annular" includes circular, ovoid, as well as other rounded shapes. The frame 110 may be configured to change shape, size, and/or configuration. For example, the frame 110 may assume various shapes, sizes, configurations etc. during different phases of deployment such as during pre-delivery, delivery, tissue engagement, and cinching.

According to one embodiment, the elongate body 112 may have a length at least about 7 cm and at most about 20 cm (corresponding to the circumference of the annulus at which the elongate body is to be implanted, which circumference varies depending on patient and disease state), a width of at least about 1 mm and at most about 10 mm and a thickness of at least about 0.02 mm and at most about 2 mm, although the disclosure is not so limited. It is appreciated that other embodiments of a frame 110 having an elongate body 112 with a length sufficient to be disposed about a treatment location, such as but not limited to a mitral valve, having a width and thickness selected to provide the torsional rigidity and structural integrity to retain the valve in a reconstructed configuration and inhibit anchor pullout in the presence of chronic palpatory forces of the treatment location may be substituted herein by one of ordinary skill in the art. It will further be appreciated that the elongate body 112 may be looped around the annulus so that at least a portion of the elongate body 112 overlaps another portion, and may even loop around the annulus two or more complete loops, such that the length of the elongate body 112 may be a multiple of a circumference of an annulus at which the elongate body 112 is to be implanted.

In one embodiment, the elongate body 112 may be formed of a shaped stainless steel, a metal alloy, a shape memory material (such as an alloy of nickel titanium or other metals), plastics, polymers, composites, other suitable materials, or combinations thereof. The elongate body 112 may be threaded through a plurality of anchor housings 120, for example through a sleeve 125 of anchor housing 120, along the circumference of the valve, for example along a generally horizontal axis generally transverse to the central axis of the valve. The anchor housing may further support an anchor 130 having a distal helical portion 136. Providing cinching forces along a different axial plane than that used to apply anchoring forces advantageously increases the torsional rigidity of the frame 110, reducing the potential and impact of anchor pullout.

In one embodiment, the elongate body 112 comprises an overlapping portion 115, wherein a first end 113 of the elongate body 112 floatingly overlaps a second end 117 of the elongate body 112. A circumference of the frame 110 may be modified by varying an extent of the overlapping portion 115 of the frame. In one embodiment, the frame 110 is biased to assume a predetermined configuration having a selected circumference, such as having a diameter slightly smaller than the idealized annulus diameter so that the leaflets coapt, for example in the range of 20 mm. In the predetermined configuration, the freely floating overlapping ends of the elongate body 112 may move freely within the anchor housing sleeves 125, enabling a degree of expansion and contraction of the frame in the presence of chronic palpatory forces while retaining valve reconfiguration. Such an arrangement minimizes the strain and fatigue experienced by the implant due to chronic palpatory forces, improving implant efficacy.

Figure 2:
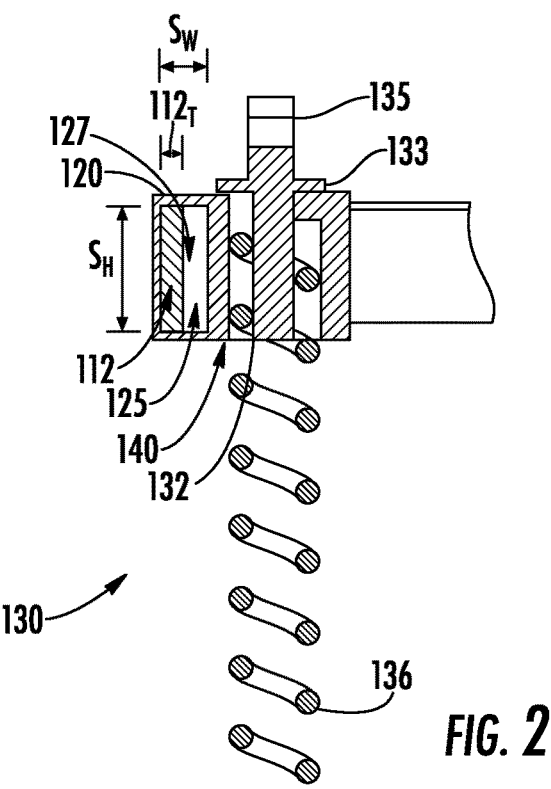
FIG. 2 is a cross-sectional view of an anchor housing configured to support a frame as disclosed herein.

FIG. 2 depicts a cross-sectional view of the anchor housing 120 including a bore 140 extending therethrough. The anchor housing may be formed from metallic materials and/or polymers with sufficient structural integrity for supporting anchors for driving into the heart annulus. The material may also be chosen based on biocompatibility and fatigue resistance. Material(s) could include stainless steel, Nickel-Titanium, Cobalt-Chromium, Pyrolytic Carbon, Nitinol, polymer materials (e.g., PEEK), and/or other suitable materials.

The bore 140 is configured to support an anchor 130 having a distal helical portion 136 and proximal shaft 132. The helical portion 136 includes a distal tip that may be a sharpened point configured to pierce tissue. The proximal shaft 132 may be solid or hollow. In various embodiments, the proximal shaft 132 and helical portion 136 may be comprised of the same or different materials. The proximal shaft 132 may be cylindrical in shape. In some embodiments, the shaft 132 may be partly cylindrical, rounded, segmented, other shapes, or combinations thereof.

In various embodiments the proximal shaft 132 and/or helical portion 136 of the anchor 130 may be made of a suitable biocompatible metal alloy such as stainless steel, cobalt chromium, platinum iridium, nickel titanium, other suitable materials, or combinations thereof. Each anchor 130 may be at least about 10 millimeters (mm) and at most about 15 mm in total axial length. In some embodiments, the anchors may be shorter or longer than 10 mm to 15 mm in axial length. By "total" axial length it is meant the axial length of the anchor 130 from the end of the distal penetrating tip of the helical portion 136 to the opposite, proximal end of the proximal shaft 132. The helical portion 136 may be at least about 6 mm and at most about 12 mm in axial length, e.g., in an axial direction. In some embodiments, the helical portion 136 of the anchor 130 may be shorter or longer than 6 mm to about 12 mm in axial length. The proximal shaft 132 and/or other non-helical portions of the anchor may be at least about 1 mm and at most about 10 mm, such as at most about 5 mm, in axial length. In some embodiments, the helical diameter range may be at least about 0.127 mm (0.050") and at most about 0.203 mm (0.080"), and the pitch may be about 0.076 mm (0.030") and at most about 0.203 mm (0.080"), such that the coil pitch angle is about twenty (20) degrees (e.g., at least about 15 degrees and at most about 30 degrees).

In one embodiment, at least a portion of a proximal end of the helical portion 136 may be wrapped around a distal end of the proximal shaft 132. In some embodiments, the helical portion 136 may be mechanically attached to the proximal shaft 132, such as by interference or friction fit, with fasteners, adhesives, bands, other suitable means, or combinations thereof. In some embodiments, the helical portion 136 may be integral with the proximal shaft 132, for example formed from the same monolithic piece of material.

The proximal shaft 132 is shown to include a coupler 135 at its proximal end. The coupler 135 may be integral with the proximal shaft 132 or a separate part attached thereto. The coupler 135 is configured for mated coupling to a drive coupler of a drive tube (not shown), that may be actuated to drive the anchor 130 into tissue, for example through distal rotation of the anchor 130 through the bore 140 of the anchor housing 120. In one embodiment, the proximal shaft 132 may include one or more flanges 133, which extend radially from the proximal end of the proximal shaft 132. A circumferential extent of the flanges 133 may be selected such that the flanges 133 inhibit further translation of the anchor 130 through the bore 140 of the anchor housing 120.

In some embodiments, the bore 140 may include grooves disposed on at least a portion of an internal wall of the bore, or may otherwise be threaded to engage turns of the anchor 130 as it is driven through the bore 140 into tissue. In some embodiments, at least a portion of an internal wall of the bore 140 is unthreaded, providing a free spin area for the anchor 130, wherein, when distal translation of the anchor 130 is impeded by engagement of the flanges 133 of the proximal shaft 132 with the anchor housing 120, the anchor 130 may continue to spin, pulling together the anchor housing 120 and tissue to improve implant affixation. In one embodiment, the anchor housing 120 may include a sleeve 125 through which the elongate body 112 passes so that the anchor housing 120 is configured to slideably translate along the elongate body 112. For example, in some embodiments the passage 127 within the sleeve 125 may have a height $S_H$ (FIG. 2) that exceeds the width W (FIG. 3A) of the elongate body 112, and a width $S_W$ (FIG. 2) that exceeds the thickness T (FIG. 3A) of the elongate body 112. In some embodiments, the width $S_W$ of the sleeve passage 127 may exceed a multiple of the thickness T of the elongate body 112, to accommodate multiple, overlapping turns of the elongate body through the sleeve, for example when the elongate body is in a compressed or cinched state as will be described in more detail later herein. For example, in some embodiments the sleeve passage 127 may have a height at least about 1 mm and at most about 10 mm, and a width at least about 0.5 mm and at most about 3 mm.

Figure 3A:
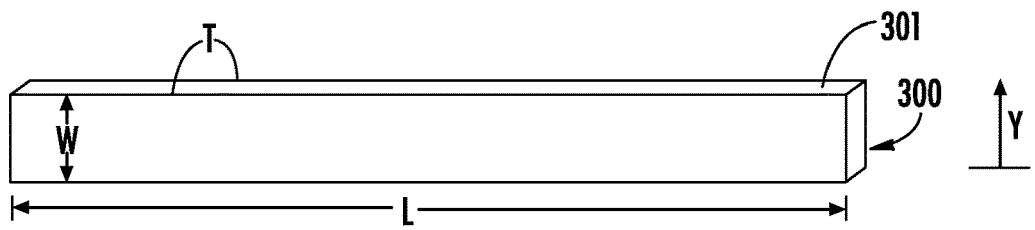
FIGS. 3A-3F illustrate various embodiments of elongate bodies that may be used as a frame of an implant disclosed herein.

FIG. 3A illustrates one embodiment of an elongate body 300 in an unshaped form that may be used to form an annular frame such as that disclosed herein. The elongate body 300 of FIG. 3A is generally rectangular in shape, having width W that extends perpendicularly along the Y axis from its length L. As mentioned above, the elongate body may be formed of stainless steel, nitinol, or similar material, and may be bent to an annular (circular, ovoid) formation having overlapping ends, allowing the elongate body to function similar to the mainspring of a watch. The frame is shown in FIG. 3A to have a fairly uniform width W and thickness T over its length L, although this is not a requirement. It may be desired to have variable torsional stiffness based on the location of the variable tissue around the annulus. For example, in some embodiments the width W or thickness T may vary over the length L, for example being wider in those portions that thread the anchor housings, and narrower in between, or vice versa. The thickness T may vary depending upon where the edges of the frame overlap, for example being thinner in overlapping sections to facilitate translation of the multiple portions of elongate body as they thread through the anchor housing.

In one embodiment, the elongate body 300 may be cut from a sheet of stainless steel or nitinol, and, as such, the edges, such as edge 301, may have a propensity to cut into adjacent tissue. Accordingly, it may be desired to round out or otherwise blunt the edges of the elongate body to reduce the potential of trauma to nearby tissue. For example, in some embodiments the edges, such as edge 301, may be angled or rounded to reduce the potential for tissue trauma.

Figure 3B:
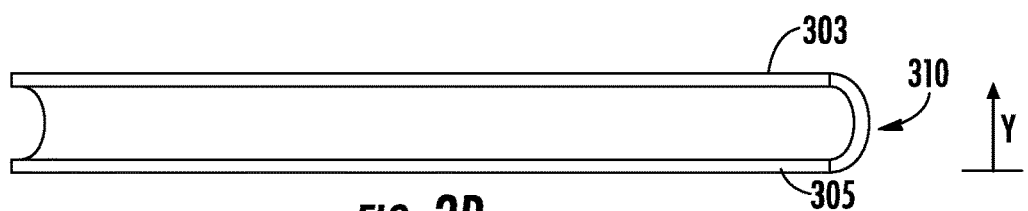
Figure 3C:
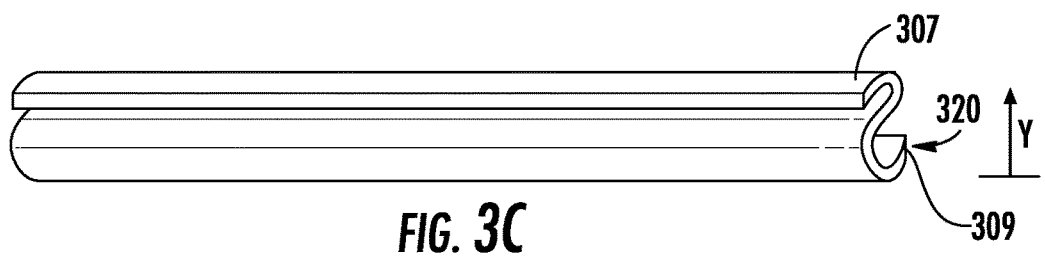
Figure 3D:
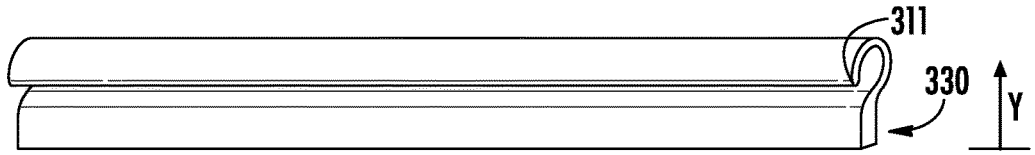

In other embodiments, such as shown in FIGS. 3B-3D, rather than, or in addition to, rounding the edges 301 of the elongate body, the elongate body may be formed such that one or both edges deflect away from the Y axis to reduce the potential for impact between the edge(s) and tissue. The degree of deflection is a matter of design choice, and may be, for example, at least about 5 degrees or less and at most about 180 degrees or more.

For example, in FIG. 3B, the elongate body may be curved so that both edges 303, 305 deflect away from the Y axis towards each other, forming a generally rounded elongate body which minimizes trauma to surrounding tissue. FIG. 3C illustrates an elongate body 320 wherein edges 307, 309 each deflect away from the Y axis in opposing directions, forming a generally S-shaped body that reduces or blunts edge trauma to tissue. FIG. 3D illustrates an elongate body 330 wherein one of the edges 307 is shown curved away from the Y axis, for example to protect neighboring tissue.

Figure 3E:
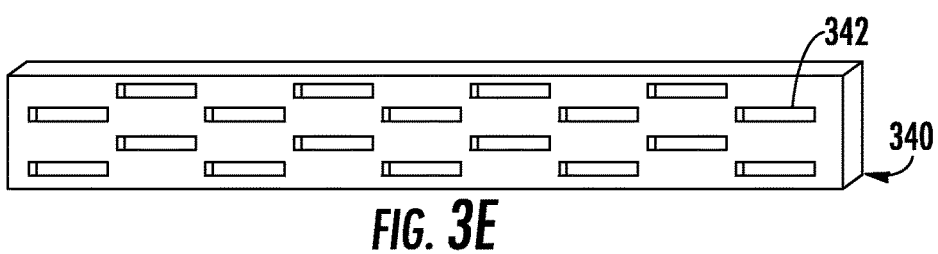
Figure 3F:
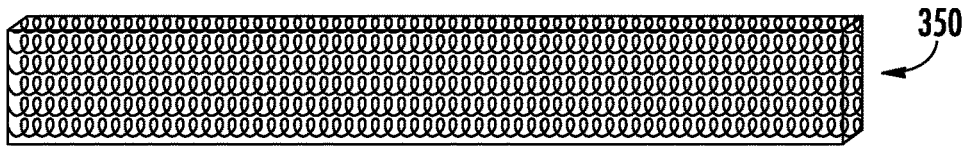

The elongate body may further be formed to distribute stresses to reduce potential for device fracture. For example, as shown in FIG. 3E, an elongate body 340 may be formed with one or more stress distribution features, including, for example slots 342 or other mechanisms, such as pores or slits, which act to distribute localized stresses and strains more effectively throughout the elongate body 340. In some embodiments, for example as shown in FIG. 3F, portions of, or the entire, elongate body 350, may be formed of a multi-coil braid or braids (e.g., a single braid made of multiple coils, multiple braids each made of single or multiple coils, multiple braids made of multiple coils in parallel, etc.) which act naturally to dampen chronic stresses while providing a flexible, strong, implant solution.

It is appreciated that the elongate body may take many forms, and that the disclosed embodiments are meant to be representative and not exhaustive of alternative embodiments. For example, in various embodiments, as described later herein, the elongate body may include additional features, such as grooves, disposed along at least a portion of the elongate body. The grooves may interact with gears within the anchor housing to adjust frame circumference. In some embodiments, the elongate body may further include features that assist in epithelial ingrowth, such as pores, surface texture, and the like. In some embodiments, the elongate body may include a drug-eluting coating to resist infection and/or aid ingrowth. In addition, it is appreciated that the elongate body may be constructed of a variety of materials which aid in stress distribution and may be formed in a variety of manners to reduce or blunt interaction between sharp surfaces and tissue.

However, according to one aspect, the various embodiments of elongate bodies may be constructed to be biased to assume an annular configuration having an adjustable circumference. The circumference may be minimized through compression of the frame to enable the implant to be deployed via a delivery catheter to a treatment site, and the circumference may be maximized through expansion of the frame for anchoring the implant about a valve treatment site.

For example, FIGS. 4A-4D illustrate various configurations of one embodiment of a frame comprising an annular elongate body threaded through a plurality of anchor housings. It should be noted that although eight anchor housings are illustrated, the disclosure is not limited to an eight anchor housing implant; rather, implants having as few as two and as many as 16 or more anchor housings are considered within the scope of this disclosure.

Figure 4A:
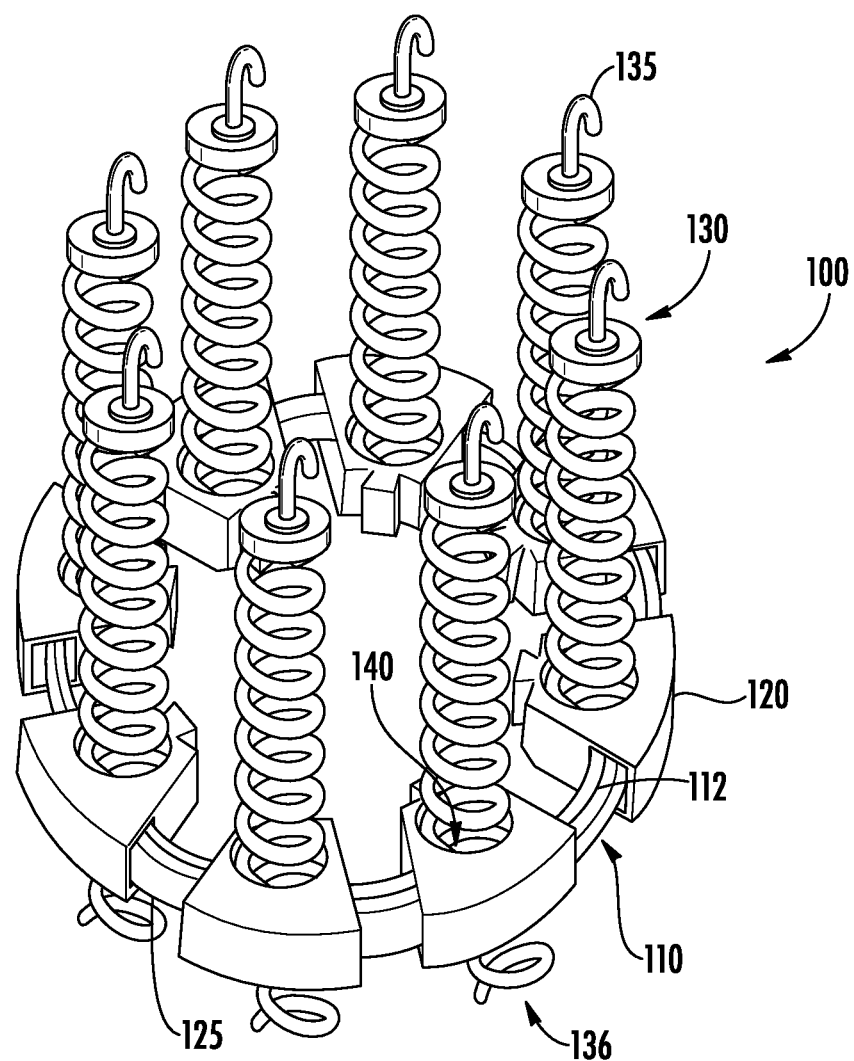
FIGS. 4A-4D illustrate the implant in various configurations that may be used as part of a valvular repair method as disclosed herein.

FIG. 4A illustrates the implant 100 of FIG. 1 in a compressed configuration, for example when the implant 100 is disposed within a distal end of a delivery catheter and delivered to a treatment site. In the pre-deployed state, the anchors 130 extend proximally from the bore 140 of the anchor housing 120, wherein the distal helical portions 136 of the anchors 130 are generally disposed within the bore 140 of the anchor housing 120 to reduce interference during delivery. Drive tubes (not shown for purposes of clarity), may be coupled to couplers 135 of the anchors, for driving the anchors 130 through the bores 140 once the implant is positioned at a treatment site. As shown in FIG. 4A in the compressed configuration of the frame 110, the elongate body 112 wraps multiple times over itself through the sleeves 125 of the anchor housings 120.

Figure 4B:
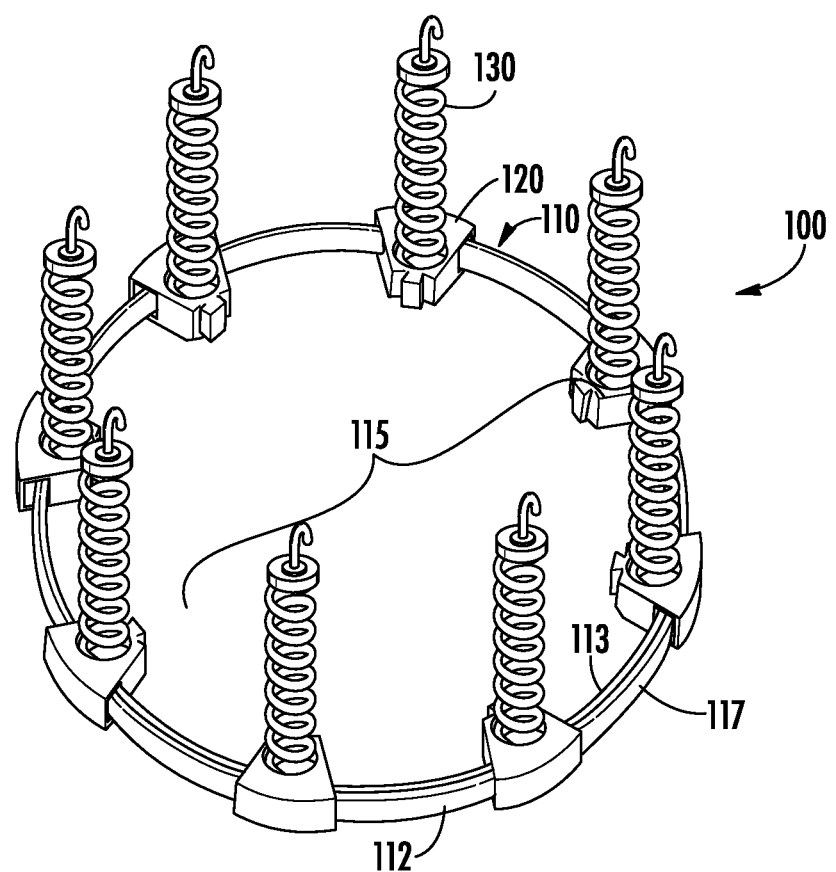

FIG. 4B illustrates the implant 100 once released from the delivery catheter. As in FIG. 4A, pre-deployment, the anchors 130 generally extend proximally from the anchor housings 120 to reduce interference during implant placement. In one embodiment, the frame 110 of the implant 100, upon release, assumes a predetermined configuration having a predetermined circumference, wherein the predetermined circumference may be commensurate with a circumference of a healthy valve which the implant 100 is to treat. For example, in FIG. 4B the predetermined configuration produces an overlapping portion 115, where floating ends 113, 117 of the elongate body 112 overlap, spanning five anchor housings 120. In one embodiment, the circumference may be, for example 20 mm, although it is appreciated that the circumference may vary depending upon the particular anatomy to be treated, the age, size, and/or gender of a patient to be treated, and/or a diseased state of the anatomy to be treated. Accordingly, the disclosure is not limited to a particular predetermined biased circumference.

Figure 4C:
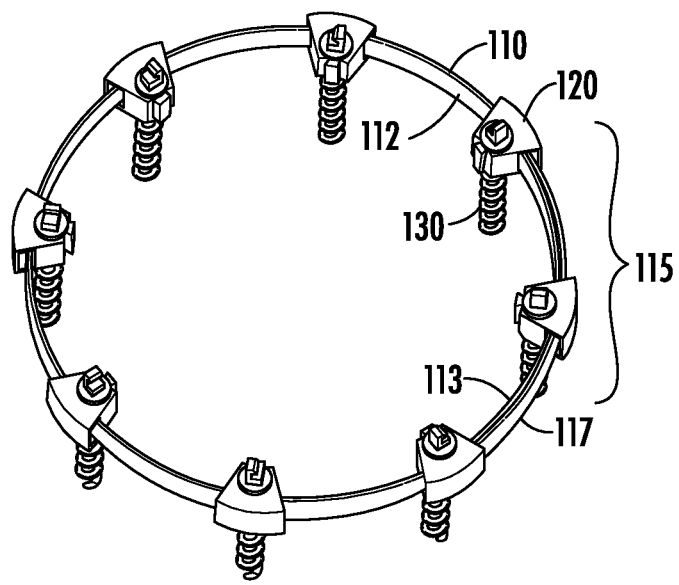

Referring now to FIG. 4C, because the predetermined circumference is that of a healthy valve, in some embodiments the frame 110 may be expanded prior to anchoring the frame 110 to tissue. As mentioned above, the floating ends 113, 117 of the elongate body 112 enable expansion and contraction of the frame 110. Expansion of the frame may be achieved in a variety of manners; for example, in one embodiment, a balloon or other expandable device (not shown) may be disposed within the delivery catheter, advanced to the center of the frame 110, and expanded to concomitantly expand the circumference of the frame 110. FIG. 4C illustrates a frame 110 that has been so expanded. As shown in FIG. 4C, the extent of the overlapping portion 115 is reduced by expansion of the frame 110 spanning only three anchor housings 120. Once the frame 110 has been expanded, the anchors 130 may be driven through the anchor housings 120 into tissue.

Figure 4D:
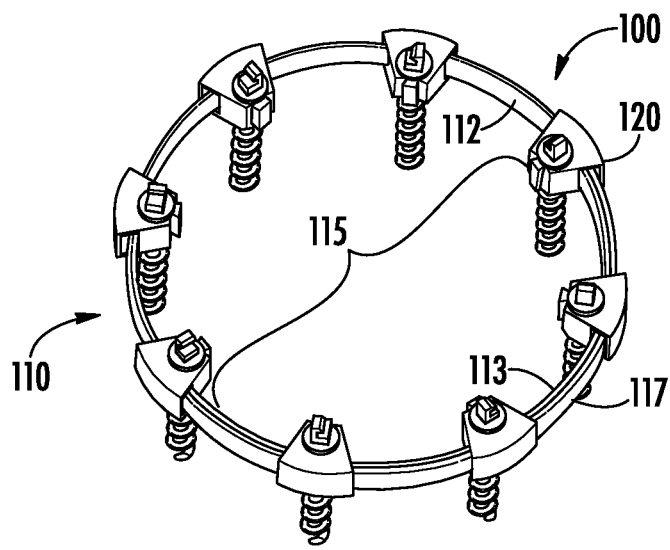

Once the anchors 130 are driven into tissue, the expansion mechanism may be released, enabling the frame 110 to return to its predetermined, cinched configuration as shown in FIG. 4D. In the cinched configuration, the overlap 115 of the ends 113, 117 of the elongate body 112 returns to span five anchor housings. As described above, in one embodiment, one or both ends of the elongate body may be left to float freely through the sleeves, enabling expansion and contraction of the frame 110 during chronic use and reducing stresses upon the implant 100.

According to one aspect, it is recognized that in some embodiments it may be advantageous to determine a method to customize the circumference of the frame to address the particular needs of a patient and/or diseased tissue state. Accordingly, in various embodiments mechanisms are provided to adjust and/or retain an extent of overlap of the ends of the elongate body.

For example, FIGS. 5A-5C illustrate one mechanism that may be used to set or secure a circumference of a frame, for example to minimize expansion and/or contraction of the frame in the presence of chronic forces by inhibiting translation of the elongate body through the sleeves of the anchor housings. An anchor housing 520 is shown to include a bore 540 extending therethrough configured to support an anchor 530 having a proximal shaft 532 and a distal helical portion 536. An anchor sleeve 525 has a passage 527 extending through the anchor housing 520 at an angle transverse to (e.g., generally perpendicular to) the anchor bore 540. An elongate body 512, shown in cross section, extends through the sleeve passage 527 along an axis generally perpendicular to the axis of the bore 540. A wall 545 separates the anchor sleeve passage 527 from the bore 540 to minimize interference between the anchor 530 and the elongate body 512.

In one embodiment, a retention mechanism for inhibiting translation of the elongate body 512 through the sleeve 525 includes an anchor shaft 532 including a cam lock having one or two cam arms 550, 552. In an open configuration, the cam arms 550, 552 are disposed about the anchor 530 in a manner that reduces interference with the anchoring process to allow adjustment of the elongate body 512. In one embodiment, in an open configuration, the cam arms lie generally flush against the shaft 532. In some embodiments, in an open configuration the cam arms may be disposed (e.g., stowed) within a hollow portion of the proximal shaft 532 or may wrap around the proximal shaft. Other implementations where the cam arms are disposed about the proximal shaft in a manner that does not interfere with driving the anchors into tissue are considered within the scope of this disclosure.

In some embodiments, when the frame has been cinched, the cam lock may be used to retain the elongate body within the anchor housing, to inhibit further translation of the elongate body through the anchor housing to secure the cinched circumference. For example, in FIG. 5B when the frame has been adjusted to a desired circumference, such as the cinched circumference or an adjusted circumference, the cam lock may be actuated, for example by rotating shaft 532 to adjust the position of the cam 550, 552 relative to the elongate body 512 to close the cam. When actuated, the cam arms 550, 552 extend through openings 547 in the wall 545 separating the bore 540 from the sleeve passage 527, urging the elongate body 512 towards an internal sidewall 526 of the sleeve passage 527, inhibiting further translation of the elongate body 512 through the sleeve, such as illustrated in FIG. 5C.

In various embodiments, a retention mechanism (such as the cam lock) may be included in a single anchor housing 520, in multiple anchor housings 520, or in all anchor housings 520 of the implant.

Figure 6A:
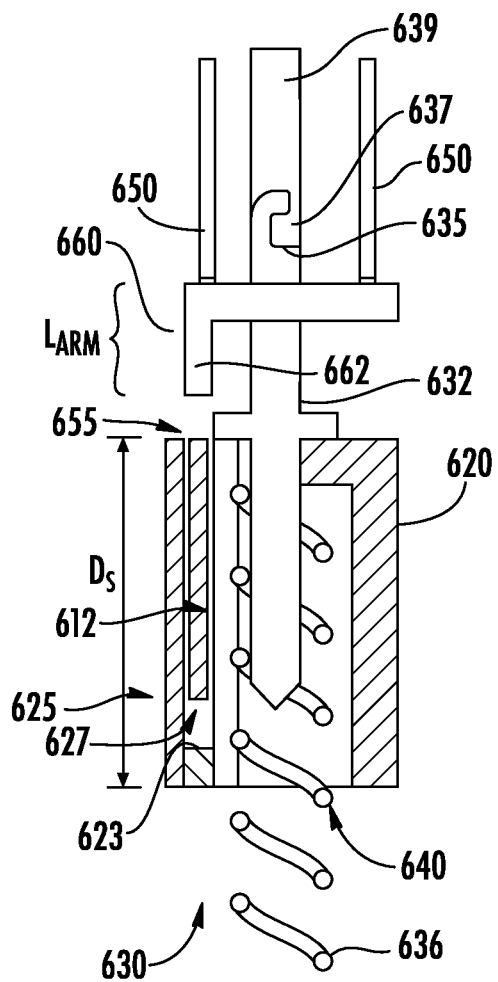
FIGS. 6A and 6B are cross-sectional views of an anchor housing illustrating one embodiment of a frame retention mechanism as disclosed herein.
Figure 6B:
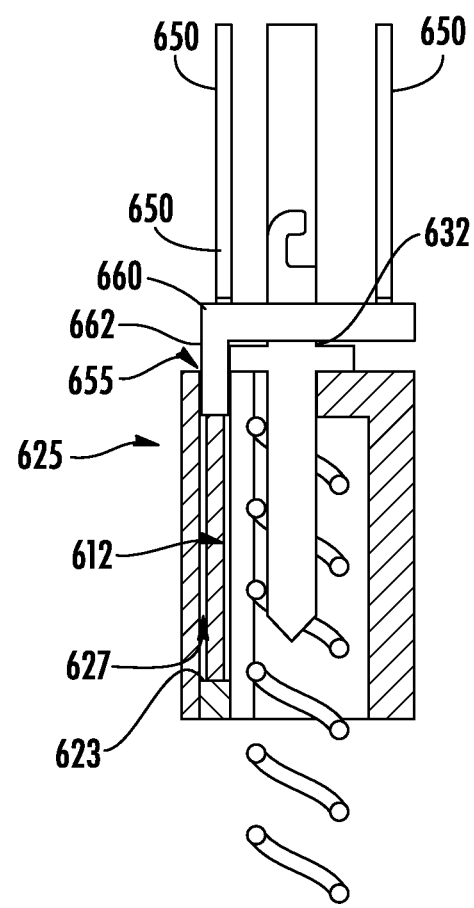

FIGS. 6A and 6B illustrate an alternate embodiment of a retention mechanism that may be provided in one or more anchor housings 620 of implants disclosed herein. In FIG. 6A, an anchor housing 620 is shown in cross-section to include a bore 640 configured to support an anchor 630 having a proximal shaft 632 and a distal helical portion 636. The proximal shaft 632 may include a coupler 635 configured to matingly engage with a coupler 637 of a drive shaft 639, where rotation of the drive shaft 639 translates the anchor 630 through the bore 640.

The anchor housing may also include a sleeve 625 with a passage 627 extending therethrough along an axis transverse to (e.g., generally perpendicular to) the axis of the bore 640, the sleeve positioned and configured for translatably supporting an elongate body 612 of an implant frame. In one embodiment, an opening 655 extends through the proximal surface of the anchor housing 620 into the sleeve 625.

A ledge 660 is shown disposed about the proximal shaft 632. The ledge 660 extends radially outward from the proximal shaft 632. An arm 662 extends distally from the ledge and is positioned over the opening 655 of the anchor housing 620. In one embodiment, the arm 662 is sized to slideably advance into the opening 655 of the anchor housing. A length $L_{ARM}$ relates to a width of the elongate body 612 (FIG. 3A) and a depth/height $D_S$ of the sleeve 625 and is selected to be sufficient to enable the arm 662 to push the elongate body 612 against a distal interior wall 623 of the sleeve 625 when the arm 662 is advanced into the opening 655 (e.g., to create interference with the elongate body 112 to induce a clamping load). In one embodiment, advancement of the ledge 660 over the proximal shaft 632 is enabled by distal translation of a push tube 650 of the proximal shaft 632 following distal translation of the anchor 630 through the bore 640.

For example, FIG. 6B illustrates an anchor housing 620 wherein the push tube 650 has been distally advanced to push the ledge 660 distally over the proximal shaft 632, thereby moving the arm 662 into the opening 655. Distal advancement of the ledge 660 and arm 662 causes the arm 662 to trap the elongate body 612 between the arm 662 and the distal interior wall 623 in the sleeve 625, inhibiting translation of the elongate body 612 through the sleeve 625 to set or secure a frame circumference.

Figure 7:
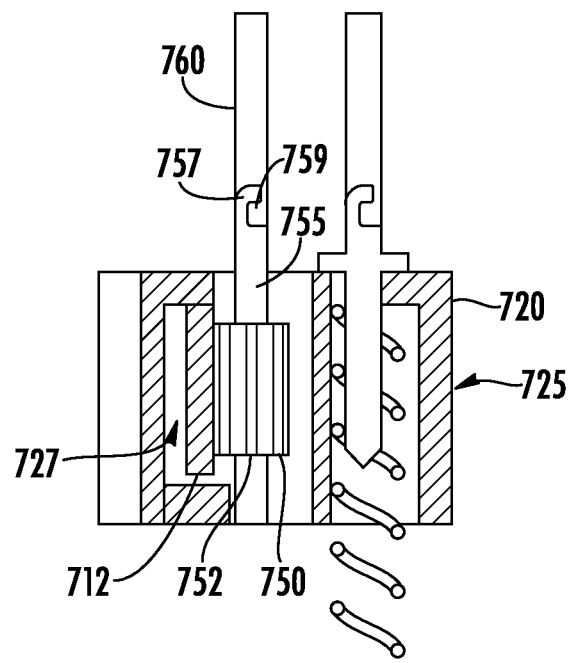
FIG. 7 is a cross-sectional view of an anchor housing illustrating one embodiment of a frame adjustment mechanism as disclosed herein.

In addition to anchor housings that include retention mechanisms, implants such as those disclosed herein may additionally or alternatively incorporate anchor housings that enable frame circumference adjustment. FIG. 7 illustrates an anchor housing 720 including one embodiment of a circumference adjustment mechanism, for example including a gear 750. In one embodiment, the gear 750 may be coupled to a shaft 755 having a proximal coupler 757 that interacts with a coupler 759 of a drive shaft 760. Rotation of the drive shaft 760 rotates the gear 750. In one embodiment, the elongate body 712 may include grooves disposed on one or more surfaces, the grooves configured to interact with teeth 752 of the gear 750 for controlled translation of the elongate body 712 through the sleeve passage 727 in the sleeve 725 of the anchor housing 720 in response to rotation of the gear 750.

Figure 8:
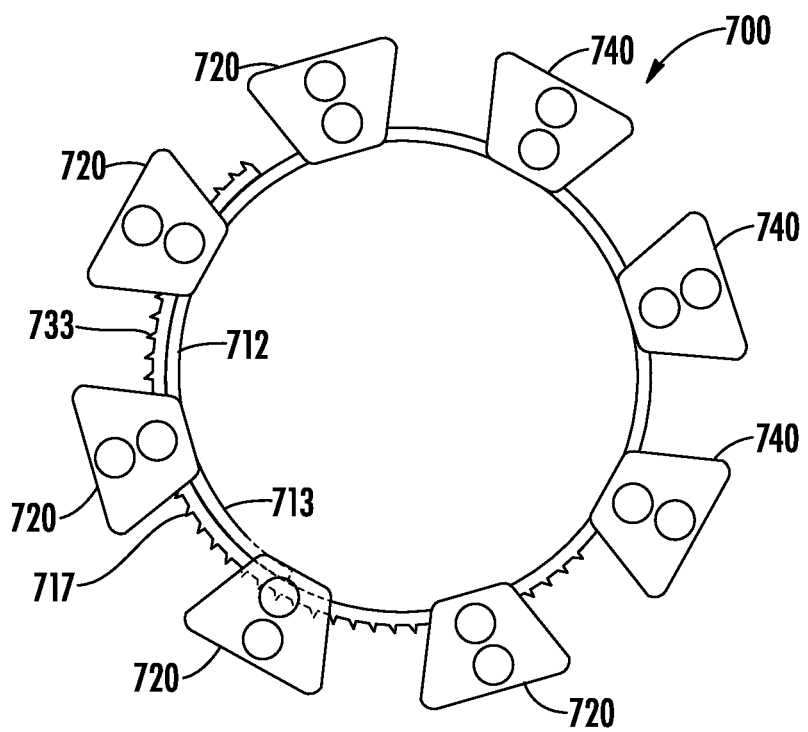
FIG. 8 is a perspective view of one embodiment of an implant including adjustment mechanisms as disclosed herein.

FIG. 8 is a top down view of one embodiment of an implant 700 including a plurality of anchor housings 720 including gear based adjustment mechanisms such as described with regard to FIG. 7. The implant 700 also includes anchor housings 740 which do not include adjustment mechanisms, and it is appreciated that in various embodiments implants may include adjustment mechanisms in one, multiple, or all anchor housings. In FIG. 8, anchor housings 740 with adjustment mechanisms are disposed along that portion of the implant having overlapping ends 713, 717, enabling the adjustment mechanisms of the anchor housings 740 to adjust the extent of overlap.

In FIG. 8, the elongate body 712 is shown to include grooves 733 disposed over at least a portion of the elongate body 712, along a surface of the elongate body that is exposed to the gears of the housings 720. While FIG. 8 illustrates grooves disposed over only a portion of the elongate body, it is appreciated that in various embodiments for various reasons, such as ease of manufacturing, it may be advantageous to dispose grooves over a portion, over discrete portions, or over the entire length of the elongate body, and the disclosure is not limited to any particular pattern of grooves over the elongate body.

Thus far the disclosure has described frames that include a unitary elongate body. However, the disclosure is not so limited, and in one embodiment it is appreciated that a low profile, adjustable implant may be provided using multiple, discrete elongate bodies, which may be effectively tied together to form the frame using anchor housings and individually adjusted using adjustment mechanisms such as illustrated in FIGS. 7 and 8.

Figure 9:
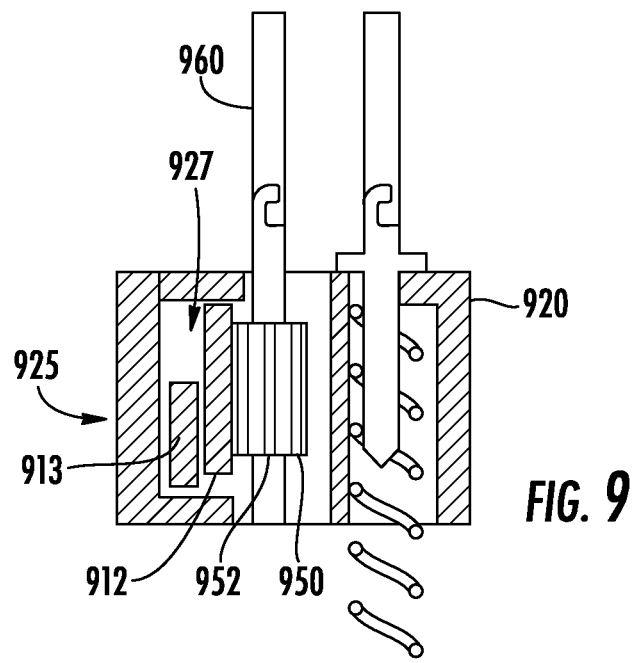
FIG. 9 is a cross-sectional views of an anchor housing illustrating one embodiment of a frame adjustment mechanism as disclosed herein.

For example, FIG. 9 illustrates an anchor housing 920 including one embodiment of a circumference adjustment mechanism, for example including a gear 950. The anchor housing 920 is similar in form and function to the anchor housing 720 of FIG. 7, however, the sleeve 925 of the anchor housing 920 is configured to support multiple elongate bodies 912 and 913, wherein elongate body 913 may originate and be internally fixed to the sleeve 925, and elongate body 912 may translate through a passage 927 in the sleeve 925, by rotation of the gear 950 by driver 960 and interaction between grooves on a surface of the elongate body 912 and teeth 952 of the gear 950.

Figure 10:
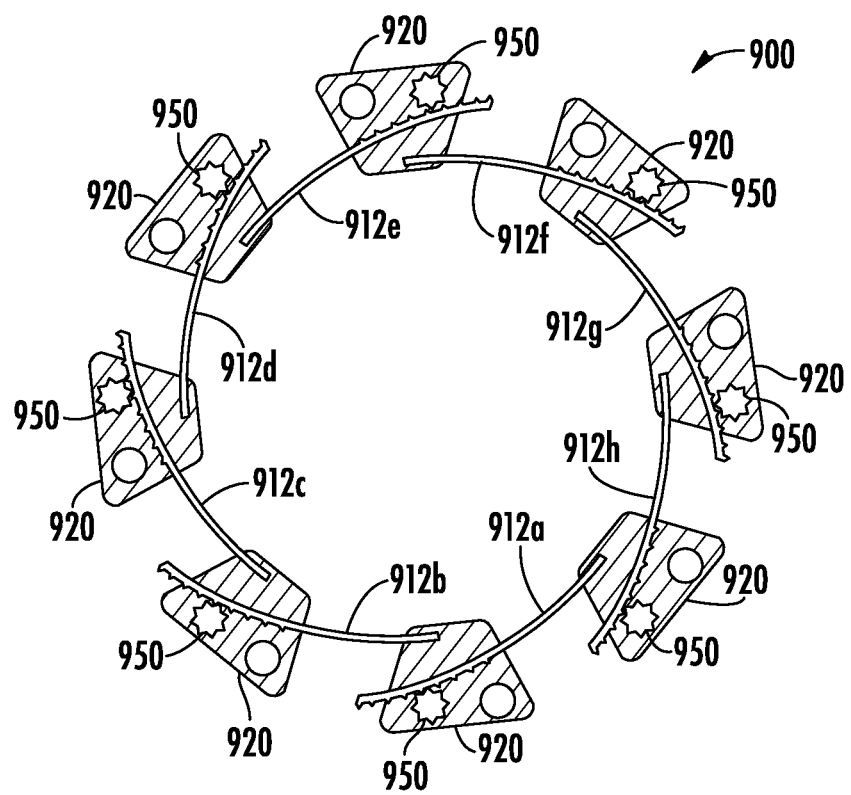
FIG. 10 is a cross-sectional view of one embodiment of an implant as disclosed herein.

For example, FIG. 10 is a top down view of an implant 900, showing anchor housings 920 in cross-sectional view. The anchor housings 920 are joined by a plurality of separately formed elongate bodies, 912*a*-912*f*, each elongate body originating at an anchor housing and translatably advanced and adjusted through an adjacent anchor housing. At least a portion of each elongate body has grooves disposed thereon to translationally engage teeth of gears 950 disposed within the anchor housings 920. With such an arrangement, gears 950 may be individually controlled to adjust spacing between anchor housing pairs, enabling full customization of the frame 900 prior to anchoring of the frame 900 to tissue. It will be appreciated that the concept of providing the elongate body in the form of a plurality of elongate bodies, each elongate body extending through a corresponding sleeve passage in a pair of adjacent anchor housings, may be applied in conjunction with any of the adjustment mechanisms disclosed herein or otherwise contemplated. An adjustment mechanism can be provided for at least one or more of the anchor housings to adjust spacing between adjacent anchor housings between which an elongate body extends.

FIGS. 11A-11E illustrate exemplary steps that may be used to deploy an implant such as that disclosed herein in various embodiments to a treatment site, such as a mitral valve. Although a transseptal delivery is illustrated, it is appreciated that the implant may be delivered in a minimally invasive percutaneous manner, such as transfemorally, transseptally, or transapically. In addition, the implant may be implanted surgically, in that it should reduce the duration of the procedure and, more particularly, the duration that the patient is on bypass. The implant may be used for mitral valve or tricuspid valve procedures.

Figure 11A:
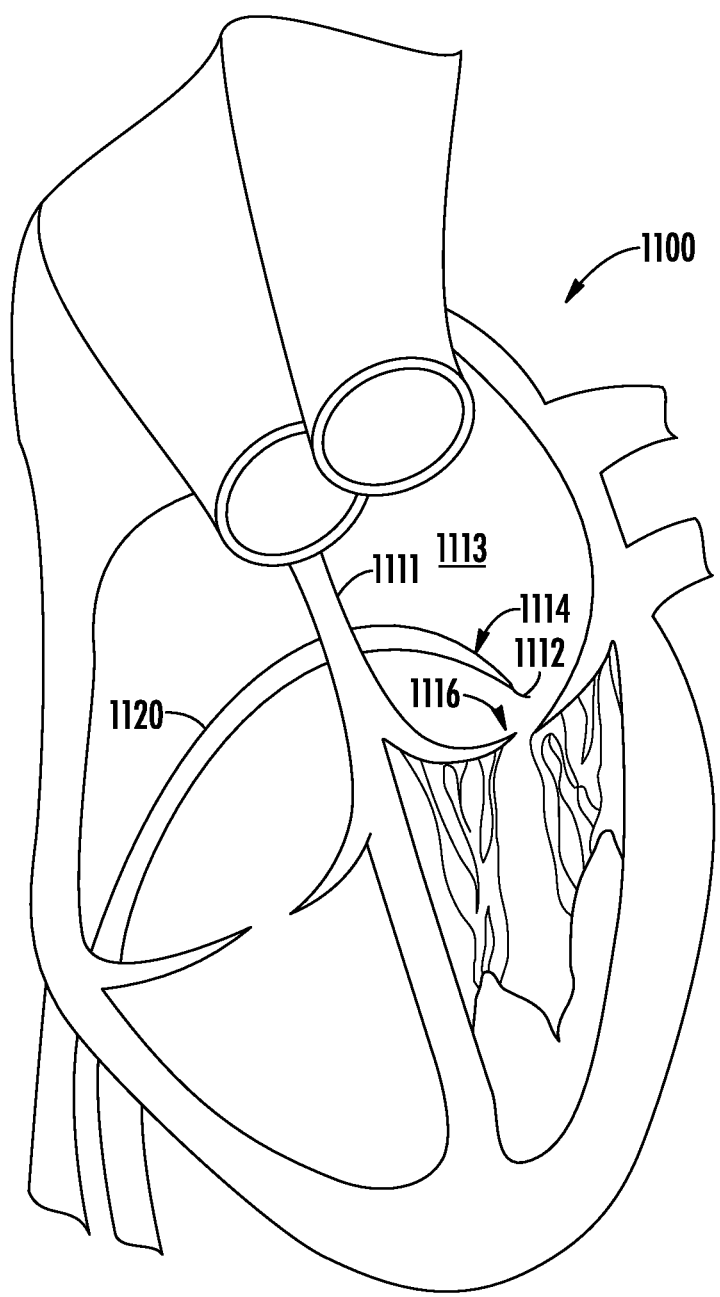
FIGS. 11A-11E illustrate an example of a method for valvular reconfiguration using an illustrative embodiment of an implant such as that disclosed herein.

In FIG. 11A a delivery catheter 1120 is deployed across the septum 1111 into the left atrium 1113 of the heart 1100 above a mitral valve 1116. The delivery catheter 1120 may comprise a braided steel core with a radiopaque sheath and a guidewire 1112 to aid in visualization. The delivery catheter 1120 may carry an implant 1114 at its distal tip.

Figure 11B:
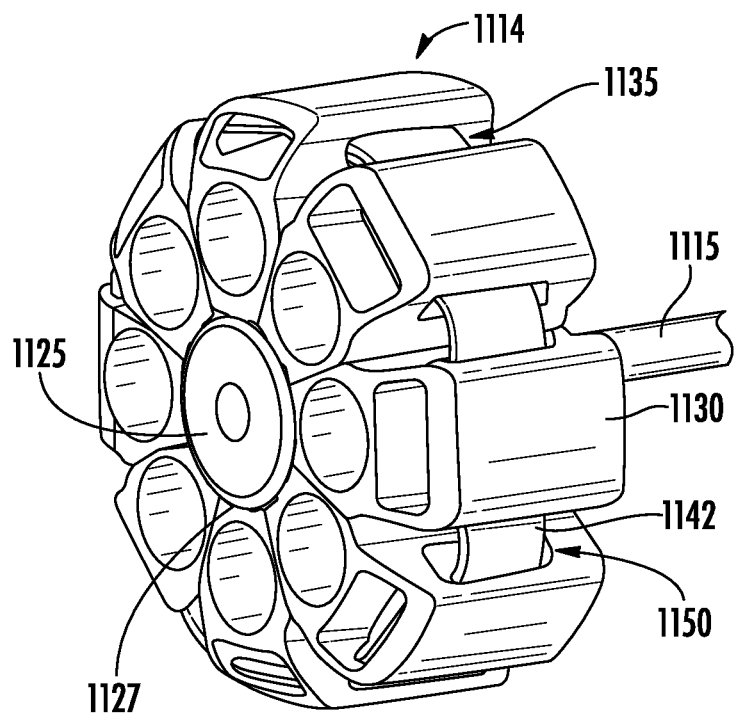

FIG. 11B illustrates the implant 1114 prior to release from the delivery catheter. In one embodiment, a shaft 1115 may include a retainer 1125 at its distal end, the retainer arranged to matingly accept tabs 1127 of the anchor housings 1130 to retain the implant 1114 in a compressed configuration for delivery. As shown in FIG. 11B, the elongate body 1142 of the frame 1150 is wrapped around itself within sleeves 1135 of the anchor housings 1130 during delivery.

Figure 11C:
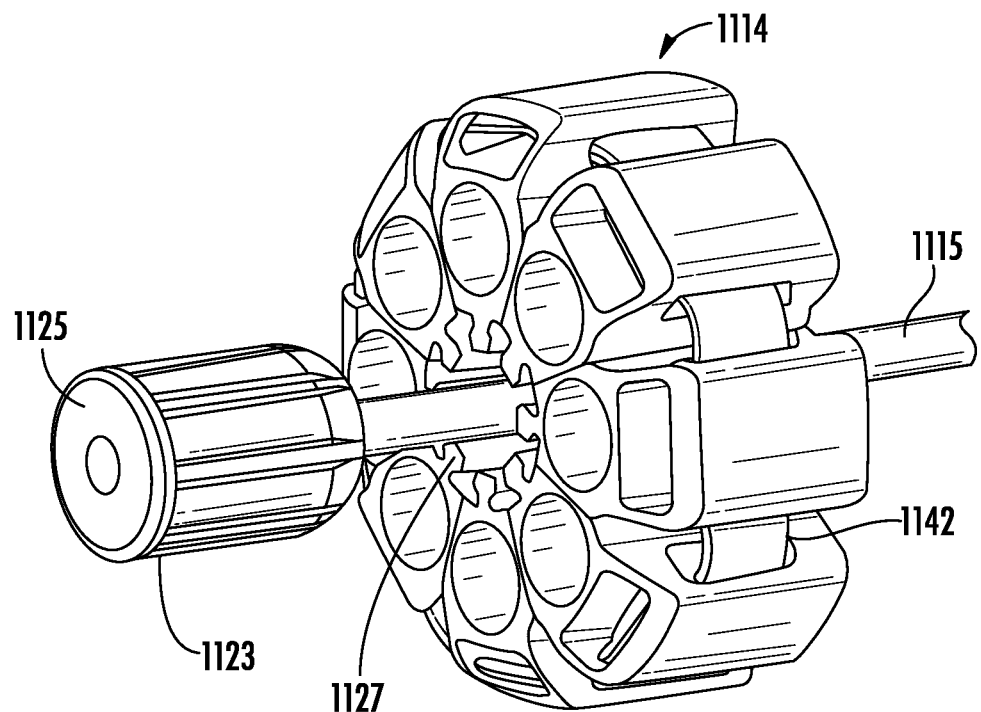

As shown in FIG. 11C, distal advancement of the shaft 1115 during deployment of the implant 1114 releases the tabs 1127 of the anchor housings 1130 from grooves 1123 of the retainer 1125, enabling the elongate body 1142 to expand to its biased circumference as described in FIGS. 4A-4D.

Figure 11D:
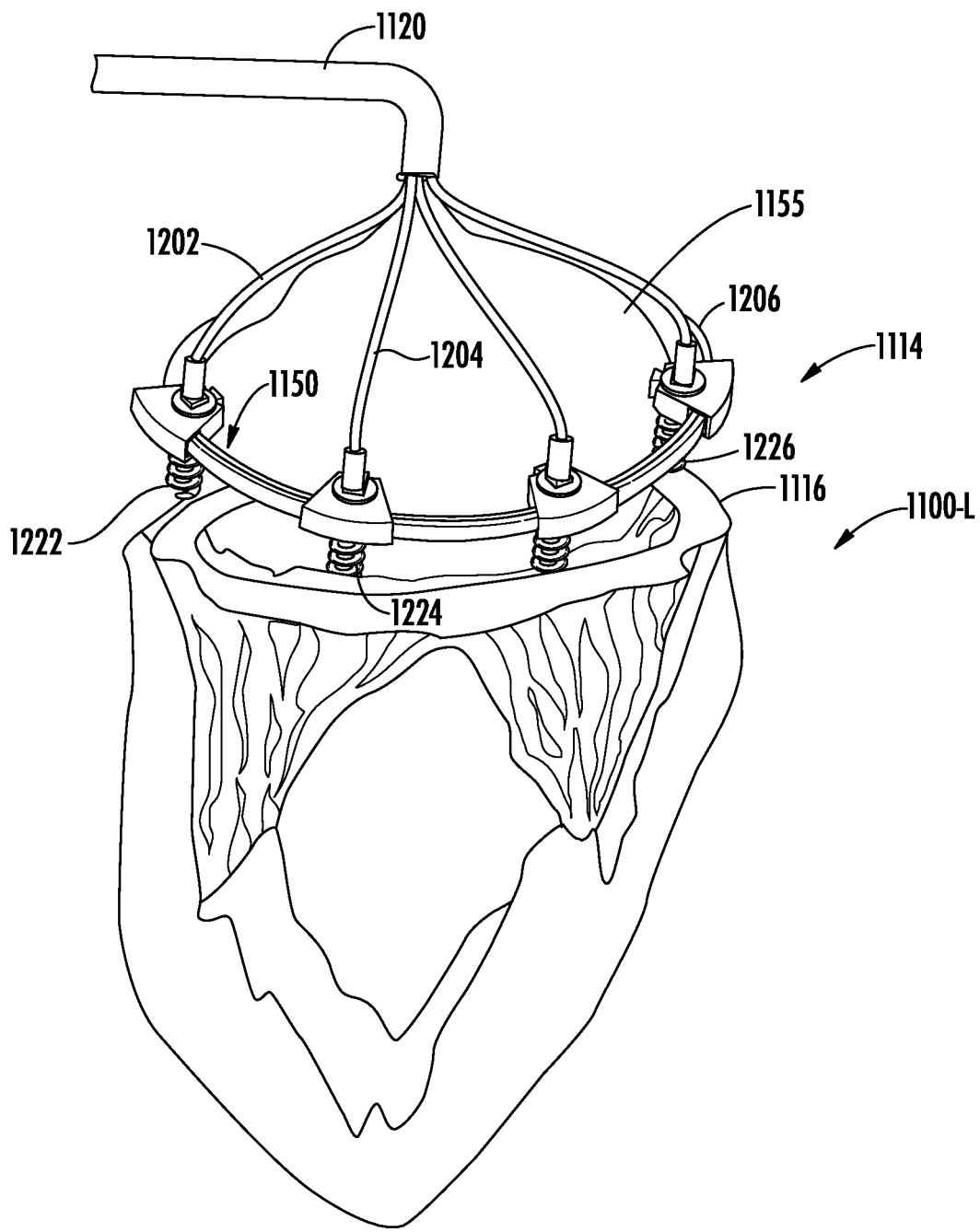
Figure 11E:
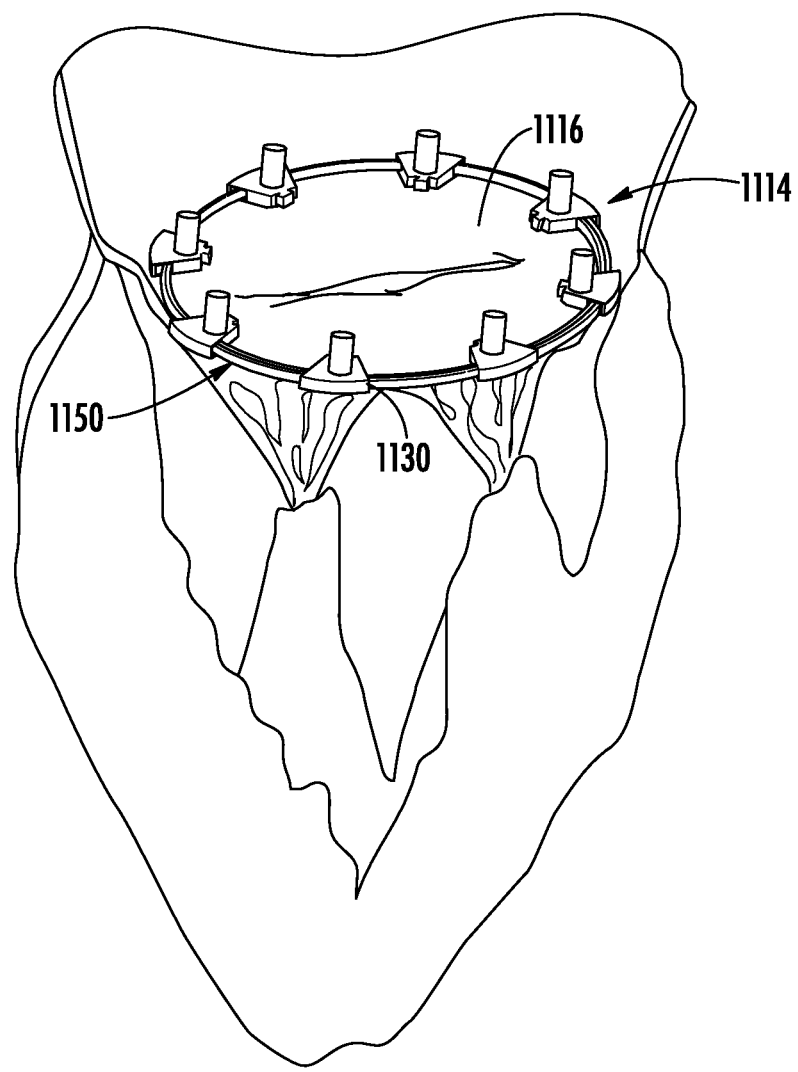

FIG. 11D illustrates the implant 1114 in an expanded state, which may be, for example an anchoring configuration. In FIGS. 11D and 11E, only the left portion 1100-L of the heart is shown, and the number of anchor housings has been reduced to four for clarity purposes. In FIG. 11D, the frame 1150 is shown expanded beyond its biased circumference using a balloon 1155 from delivery catheter 1120, to position the frame 1150 at the desired position around the mitral valve 1116, for example proximate a mitral valve annulus. The frame 1150 may then be anchored using drive tubes 1202, 1204, 1206 to drive anchors 1222, 1224, and 1226, respectively, into annular tissue.

FIG. 11E illustrates the implant 1114, anchored around the mitral valve 1116 in a cinched configuration comprising an annular reconstruction configuration. As shown in FIG. 11E, the cinching action of the frame 1150 as it returns to its biased configuration pulls together the leaflets of the mitral valve 1116, restoring valve function. The remaining implant structure 1114, including only the frame 1150 and the anchor housings 1130, provides a low profile implant capable of withstanding chronic palpatory forces.

Accordingly, a low profile implant, system and method of delivery have been shown and described. Although embodiments of the present disclosure may be described with specific reference to medical devices and systems (e.g., transluminal devices inserted through a femoral vein or the like) for selective access to heart tissue, it should be appreciated that such medical devices and systems may be used in a variety of medical procedures that require anchoring to heart tissue. The disclosed medical devices and systems may also be inserted via different access points and approaches, e.g., percutaneously, endoscopically, laparoscopically, or combinations thereof.

As used herein, the singular forms "a," "an," and "the" are intended to include the plural forms as well, unless the context clearly indicates otherwise. The terms "comprises" and/or "comprising," or "includes" and/or "including" when used herein, specify the presence of stated features, regions, steps, elements, and/or components, but do not preclude the presence or addition of one or more other features, regions, integers, steps, operations, elements, components, and/or groups thereof.

As used herein, the conjunction "and" includes each of the structures, components, features, or the like, which are so conjoined, unless the context clearly indicates otherwise, and the conjunction "or" includes one or the others of the structures, components, features, or the like, which are so conjoined, singly and in any combination and number, unless the context clearly indicates otherwise.

All numeric values are herein assumed to be modified by the term "about," whether or not explicitly indicated. The term "about," in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified. The recitation of numerical ranges by endpoints includes all numbers within that range, including the endpoints (e.g. 1 to 5 includes 1, 1.5, 2, 2.75, 3, 3.80, 4, and 5).

It is noted that references in the specification to "an embodiment," "some embodiments," "other embodiments," etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described herein, even if not explicitly shown in a particular combination, are nevertheless contemplated as being combinable or arrangeable with each other to form other additional embodiments or to complement and/or enrich the described embodiment(s), as would be understood by one of ordinary skill in the art.

The devices and/or methods disclosed and claimed herein can be made and executed without undue experimentation in light of the present disclosure. While various embodiments of the devices and methods of this disclosure have been described, it may be apparent to those of skill in the art that variations can be applied to the devices and/or methods and in the steps or in the sequence of steps of the method described herein without departing from the concept, spirit, and scope of the disclosure. All such similar substitutes and modifications apparent to those skilled in the art are deemed to be within the spirit, scope, and concept of the disclosure as defined by the appended claims.

What is claimed is:
1. An implant comprising:
a frame comprising an elongate body having an annular configuration with an adjustable circumference;
an anchor housing comprising a sleeve having a sleeve passage extending through the anchor housing along a first axis and a bore extending through the anchor housing along a second axis, different from the first axis, wherein the elongate body of the frame is translatable through the sleeve passage; and a retention mechanism configured to retain the frame at an adjusted circumference by inhibiting translation of the elongate body through the sleeve passage of the anchor housing by securing the elongate body against a portion of the anchor housing.

2. The implant of claim 1, including an anchor translatably disposed within the bore of the anchor housing.

3. The implant of claim 1, wherein the retention mechanism is configured to retain the frame at the adjusted circumference by securing the elongate body between an internal wall of the sleeve passage of the anchor housing and the retention mechanism.

4. The implant of claim 3, further comprising an anchor, wherein the retention mechanism includes a cam lock disposed about the anchor and having a locked configuration wherein a cam arm of the cam lock urges the elongate body towards the internal wall of the sleeve passage to inhibit translation of the elongate body through the sleeve passage.

5. The implant of claim 1, further comprising an anchor, wherein
the anchor comprises a proximal shaft disposed along the second axis;
the retention mechanism comprises a ledge extending radially from the proximal shaft and an arm extending distally from the ledge; and
the arm is aligned with the sleeve passage and configured to extend into the sleeve passage when the ledge is distally translated to urge the elongate body towards an end wall of the anchor housing to inhibit translation of the elongate body through the sleeve passage.

6. The implant of claim 1, wherein the elongate body comprises a ribbon frame, and the ribbon frame is comprised of stainless steel, a shaped memory alloy, a polymer or a combination thereof, the ribbon frame having a first end and a second end that overlap in the annular configuration, wherein the adjustable circumference is based on an extent of overlap between the first end and the second end.

7. The implant of claim 6, wherein the ribbon frame comprises a first compressed configuration enabling the ribbon frame to be transluminally advanced to a treatment site and an expanded configuration having an annulus repair circumference selected to position the ribbon frame about a valve annulus.

8. The implant of claim 6, wherein the ribbon frame comprises at least one blunted edge, at least one stress diffusion feature, or combination thereof.

9. An implant comprising:
a plurality of anchor housings, each anchor housing having a sleeve with a sleeve passage and a bore extending therethrough, wherein each sleeve extends through the respective anchor housing along a first axis, and each bore extends through the respective anchor housing along a second axis, different from the first axis;
a plurality of anchors, each anchor extending through one of the plurality of anchor housings, each anchor including a sharpened distal tip;
a frame comprising an elongate body extending through each sleeve of each anchor housing, the elongate body having an annular configuration configured to position the plurality of anchor housings supported by the frame about a valve annulus; and
a retention mechanism configured to retain the frame at an adjusted circumference by inhibiting translation of the elongate body through the sleeve passage of at least one anchor housing by securing the elongate body against a portion of the at least one anchor housing.

10. The implant of claim 9, further comprising a wall separating the sleeve passage from the bore in each anchor housing.

11. The implant of claim 10, wherein the elongate body is comprised of stainless steel, a shaped memory alloy, a polymer, or a combination thereof, and includes a first end and a second end that overlap in the annular configuration, wherein the circumference of the frame is based on an extent of overlap between the first end and the second end.

12. The implant of claim 9, wherein the retention mechanism is configured to retain the frame at the adjusted circumference by securing the elongate body between an internal wall of the sleeve passage of the at least one anchor housing and the retention mechanism.

13. The implant of claim 12, wherein the retention mechanism includes a cam lock disposed about the anchor in the at least one anchor housing and having a locked configuration wherein a cam arm of the cam lock urges the elongate body towards the internal wall of the sleeve passage of the at least one anchor housing to inhibit translation of the elongate body through the sleeve passage of the at least one anchor housing.

14. The implant of claim 9, wherein the plurality of anchors comprise a proximal shaft disposed along the second axis, and the retention mechanism comprises a ledge that extends radially from the proximal shaft and an arm extending distally from the ledge, the arm is aligned with the sleeve passage and configured to extend into the sleeve passage when the ledge is distally translated to urge the elongate body towards an end wall of the at least one anchor housing to inhibit translation of the elongate body through the sleeve passage.

15. A method of valvular repair comprising:
advancing a distal end of a delivery catheter to a valve treatment site, the distal end of the delivery catheter having an implant disposed therein;
releasing the implant from the distal end of the delivery catheter, wherein the implant includes an anchor housing supporting an anchor and comprising a sleeve with a sleeve passage extending therethrough along a first axis and a bore extending through the anchor housing along a second axis, different from the first axis, wherein the implant includes a frame comprising an elongate body having an annular configuration with an adjustable circumference, the elongate body translatable through the sleeve passage of the anchor housing;
expanding the frame to position the anchor housings about a valve annulus;
adjusting the circumference of the frame to an adjusted circumference;
driving a plurality of anchors into tissue of the valve annulus; and
securing the frame within and against a portion of the anchor housing to inhibit translation of the elongate body through the sleeve passage to retain the adjusted circumference of the frame.

16. The method of claim 15, wherein ends of the elongate body overlap through the sleeve passage of the anchor housing.

* * * * *